United States Patent [19]

Fischer

[11] Patent Number: 4,522,593
[45] Date of Patent: Jun. 11, 1985

[54] KNITTED GINGIVAL RETRACTION CORD

[76] Inventor: Dan E. Fischer, 10444 Dimple Dale Rd., Sandy, Utah 84092

[21] Appl. No.: 511,779

[22] Filed: Jul. 7, 1983

[51] Int. Cl.$^3$ ............................................. A61C 5/14
[52] U.S. Cl. .................................................. 433/136
[58] Field of Search ............ 433/136, 40; 128/335.5, 128/334 R, 269, 296; 132/92 A, 92 R, 93

[56] References Cited

U.S. PATENT DOCUMENTS

| | | | |
|---|---|---|---|
| 1,287,926 | 12/1918 | Ecaubert | 132/92 A |
| 3,108,357 | 10/1963 | Liebig | 128/334 R |
| 3,124,136 | 3/1964 | Usher | 128/334 R |
| 3,463,158 | 8/1969 | Schmitt et al. | 128/334 R |
| 3,540,452 | 11/1970 | Usher et al. | 128/335.5 |
| 4,137,921 | 2/1979 | Okuzumi et al. | 128/335.5 |
| 4,321,038 | 3/1982 | Porteous | 433/136 |

OTHER PUBLICATIONS

Advertising brochure of Van R. Dental Products, Inc. concerning braided retraction cord offered for sale by that company.
Advertising brochure of Gingi-Pak Laboratories concerning that company's braided retraction cord.

Primary Examiner—John J. Wilson
Attorney, Agent, or Firm—Workman, Nydegger & Jensen

[57] ABSTRACT

A gingival retraction cord having improved characteristics is advantageously constructed by a knitting process. Because of the presence of numerous interlocking loops, the knitted retraction cord is longitudinally elastic, thereby avoiding the tendency to become dislodged once packed as additional portions of the cord are packed around the margin of a tooth. The knitted retraction cord is also transversely resilient, thereby tending to better conform to the gingival sulcus.

23 Claims, 16 Drawing Figures

KNITTED GINGIVAL RETRACTION CORD

BACKGROUND

1. Field of the Invention

The present invention relates to methods and apparatus utilized in gingival tissue management during the preparation of artificial crowns and bridges. More particularly, the present invention is directed to construction and use of gingival retraction cord for retracting gingival tissue preparatory to making an impression of a tooth that has been prepared for fitting of an artificial crown.

2. The Prior Art

It has become a common dental procedure to replace a damaged or malformed crown of a tooth with an artificial crown constructed of porcelain and/or gold. A well-fitting and properly contoured artificial crown will give many years of excellent service to its wearer. An improper fit, on the other hand, will result in premature failure and detachment of the artificial crown from the tooth.

The present invention is useful in preparing a well-fitting artificial crown. However, in order to understand the present invention it is helpful to first review the process involved in fitting an artificial crown, as well as several prior art types of retraction cord presently used in the state of the art.

Figure 1:
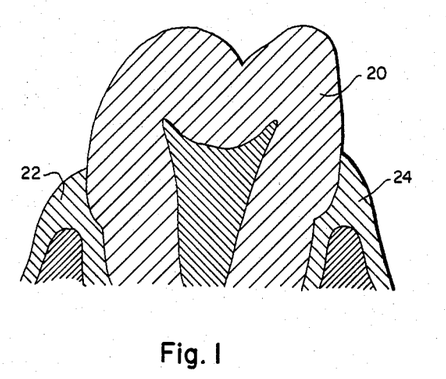
FIG. 1 is a vertical section of a typical tooth and surrounding gingival tissue.

FIG. 1 illustrates a normal tooth 20 requiring restoration by use of an artificial crown. Tooth 20 is surrounded by gingival tissue 22 and 24 (gingival tissue is commonly referred to as the "gums").

Figure 2:
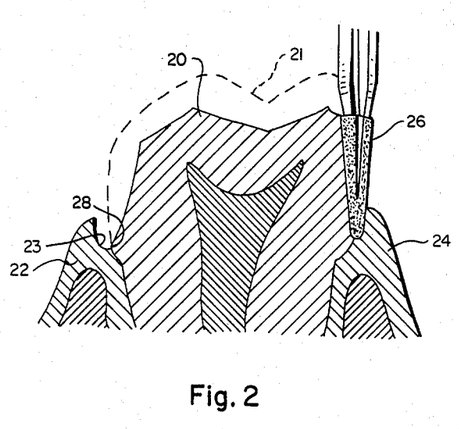
FIG. 2 is a view similar to FIG. 1 but showing the tooth after it has been suitably shaped by a high speed drill preparatory to receiving an artificial crown.

The dental practitioner first prepares the tooth to receive an artificial crown by removing portions of the tooth (shown by the broken line outline at 21) with a high-speed drill 26, as indicated in FIG. 2. The junction at which the uncut lower portion and the cut upper portion of the tooth meet is referred to as the "margin" 28. It has been found that in order to construct artificial crowns capable of remaining secured to the tooth in a physiologically sound condition for an extended period of time, it is critical to make an accurate impression in the area of margin 28. Failure to do so can result in decay around the area of the margin, or other physiological problems. Thus, premature failure of a crown is almost always due to poor marginal detail in the impression used to fabricate the crown.

Figure 3:
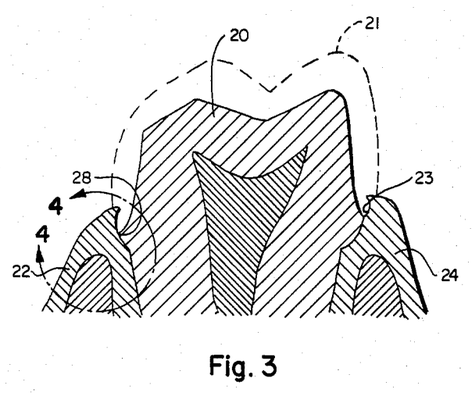
FIG. 3 is a view similar to FIG. 2 but showing the tendency of the gingival cuff to contract after completion of the shaping and prior to packing of the retraction cord.

Gingival supporting tissue 22, 24 is comprised largely of collagen fibers. Because these collagen fibers are highly elastic, the gingival cuff will begin to constrict around the margin 28 of the cut tooth almost immediately after the tooth has been shaped to receive a crown (see FIG. 3). This prevents adequate amounts of impression material from being placed around the margin 28 of the tooth 20. In addition, damage to the gingival tissue 22, 24 during cutting of the tooth 20 results in bleeding around the periphery of the tooth into the space formed between the gingival tissue 22, 24 and the tooth 20, this space generally being referred to in the art as the "gingival sulcus" 23, which is shown in FIGS. 2 and 3. This bleeding further interferes with the taking of a good impression because extravasated blood tends to prevent adequate cleaning and drying of the marginal area of the tooth prior to taking an impression and tends to displace the impression material before it can set.

Thus, the dual problems of contraction of the gingival cuff and the presence of hemorrhaging tissues make it impractical to simply take an impression following shaping of the tooth with the high-speed drill. Rather, four basic requirements have been identified for the taking of consistently acceptable impressions.

First, it is recognized that the gingival cuff must be horizontally retracted from around the marginal area of the tooth sufficient to permit an adequate bulk of impression material to be placed around the margin of the tooth. A second, and related requirement for the taking of an adequate impression is to displace the gingival tissue vertically in order to expose a portion of the tooth below the margin so that the impression will clearly indicate the location of the margin and will give good marginal detail. Third, all hemorrhage must be arrested prior to taking the impression, and fourth, the area where the impression is to be taken must be thoroughly cleaned and dried.

Figure 4:
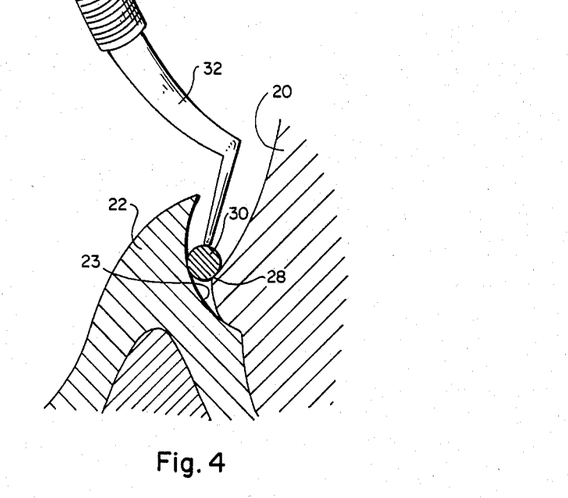
FIG. 4 illustrates the portion of FIG. 3 indicated by the line 4—4, drawn to a larger scale and showing the step of packing a length of prior art type retraction cord into the gingival sulcus.

The most common method for providing horizontal and vertical retraction is by use of retraction cord. Thus, as illustrated in FIG. 4, a length of retraction cord 30 is packed between gingival tissue 22 and the margin 28 of tooth 20 by use of an appropriate dental instrument 32.

Figure 5:
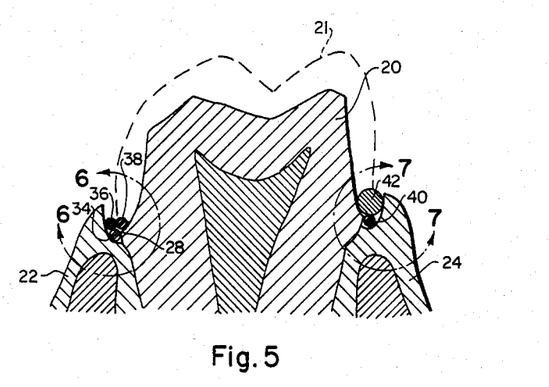
FIG. 5 is a view similar to FIG. 3 but further illustrating the use of prior art types of retraction cord to retract the gingival tissue from around the margin of the shaped tooth.
Figure 6:
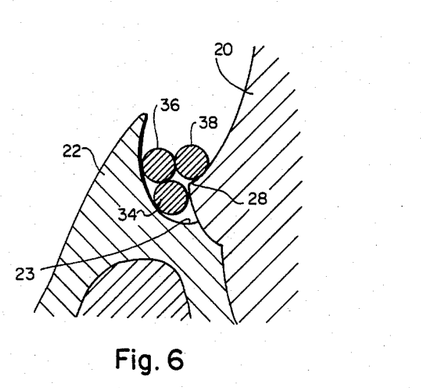
FIG. 6 is an enlarged view of the portion of FIG. 5 taken along the line 6—6.
Figure 8:
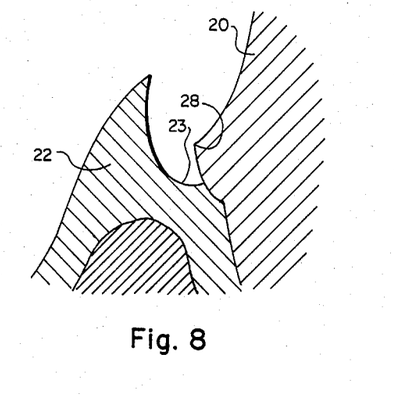
FIG. 8 is a view similar to FIG. 4 but showing the appearance of the retracted gingival tissue upon removal of the retraction cord.

It is often necessary to pack several lengths of retraction cord into the sulcus 23 in order to obtain sufficient vertical and horizontal retraction of gingival tissue. FIG. 5 illustrates two possible approaches for utilizing multiple lengths of retraction cord. Thus, on the left side of tooth 20 it is indicated that three lengths of retraction cord 34, 36, and 38 might at times be used to obtain suitable gingival retraction. As better seen in FIG. 6, cord 34 causes vertical displacement of the gingival tissue in a direction toward the root of the tooth ("apical" displacement). This permits an accurate determination of the location of the margin 28. Cords 36 and 38 are then packed side-by-side over cord 34 and margin 28 so as to cause horizontal displacement of the gingival tissue. The result of the use of retraction cord is illustrated in FIG. 8; the margin 28 of the tooth is exposed sufficiently so that it is possible to make an impression having excellent marginal detail.

Figure 7:
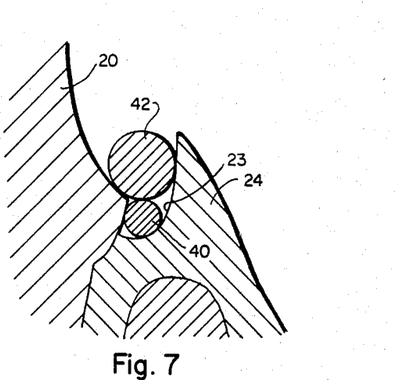
FIG. 7 is an enlarged view of the portion of FIG. 5 taken along the line 7—7.

Returning to a consideration of FIG. 5, a second approach for retracting gingival tissue is illustrated on the right side of tooth 20. (It should be understood that in actual practice only a single approach would generally be taken with respect to a single tooth; the differences between the approaches taken on the right and left sides of tooth 20 in FIG. 5 are primarily for purposes of illustration.) Thus, in FIG. 5 it may be seen that it is possible to use only two retraction cords 40 and 42 to retract gingival tissue 24 in place of the three cords 34, 36 and 38 used in retraction of gingival tissue 22. Referring to FIG. 7, which is drawn to a larger scale, it may be seen that a small cord 40 corresponding to cord 34 of FIG. 6 can be used to accomplish vertical retraction, but a single cord 42 having a diameter approximately twice that of cord 40 may be used for obtaining the necessary horizontal retraction.

As mentioned above, gingival supporting tissue is comprised largely of flexible collagen fibers. Thus, although mere mechanical retraction is effective to some extent if the gingival tissue need not be displaced for more than a very short period of time after removal of the retraction cord, in practice it is usually preferable to apply a chemical retracting agent that reduces the tendency of the gingival tissue to contract over the margin after the retraction cord is removed. This is conveniently accomplished by soaking the retraction cord in a solution containing the chemical agent prior to packing the cord into the sulcus, or by pre-impregnating the cord with a suitable chemical agent. When such a suitable retracting agent and retraction cord are used, it is possible to maintain the gingival displacement illustrated in FIG. 8 for a period of time sufficient to permit the dental practitioner to make an impression.

As mentioned above, another requirement for the taking of a good quality impression is the arresting of any hemorrhaging caused by damage to gingival tissue during shaping of the tooth. Accordingly, in addition to use of a chemical retracting agent, it has been found useful to apply a chemical hemostatic agent to discontinue blood flow from damaged blood vessels. Again, this chemical agent can be applied by soaking the retraction cord in an appropriate solution prior to placement. Typically, the same chemical agent used to assist retraction also has hemostatic properties.

For many years, the only type of retraction cord available was constructed of multi-strand twisted cotton yarn. Although this type of retraction cord has been used extensively, it has a number of significant disadvantages. First, because only short lengths of cord are used, it is not uncommon for the twisted fibers to unravel. Also, there is a tendency for the dental packing instrument 37 (see FIG. 4) to slip between the twisted fibers, thereby making packing more difficult and often resulting in damage to underlying tissue. Further, withdrawing the dental instrument after it has slipped between fibers often results in pulling the cord from its position in the sulcus. Finally, because of the tendency of the twisted-strands to rearrange themselves, there is a tendency for this type of cord to flatten, thereby reducing its effectiveness in terms of horizontal or vertical retraction.

A substitute to the use of twisted cotton cord is disclosed in U.S. Pat. No. 4,321,038 wherein the use of a braided retraction cord is described. The weaving process used in the construction of this braided cord insures that the cord maintains its structural integrity so as not to unravel; a plurality of longitudinally disposed warp strands are tightly weaved together with a plurality of transversely disposed filling strands. Because of this structural integrity, there is no tendency for the dental instrument to slip between the various fibers used in construction of the cord and the cord will maintain its shape when packed into the gingival sulcus rather than flattening out in the manner of twisted-strand retraction cord.

However, notwithstanding these advantages, the braided cord also suffers from a number of disadvantages inherent in its design since the very properties that cause it to retain its shape also have undesirable side effects. For example, braided retraction cord has very little "give" (i.e., is not very resilient in either the longitudinal or transverse dimensions). It will be appreciated from a consideration of FIG. 4 that since the braided cord 28 prevents the tip of instrument 32 from slipping between the braided-strands (not shown), and since there is relatively little give in response to the radially or downwardly directed pressure exerted on the cord 30 by instrument 32, there is a tendency for the dental packing instrument 32 to slip off the cord 30 during packing. When this happens it is not uncommon for the tip of instrument 32 to impact the gingival tissue 22 or the base of the tooth 20 in a harmful manner.

Another disadvantage when utilizing a braided cord is that when the various fibers are weaved together closely enough and tightly enough to prevent a dental packing instrument from slipping between the fibers, the spaces between fibers are quite small and the cord has a rather small capacity for soaking up and retaining liquids. This limits the amount of liquid chemical hemostatic and/or retractive agent that can be carried into the sulcus by the braided retraction cord, which in turn reduces the effectiveness of the retraction cord in effecting retraction and in arresting hemorrhage.

Yet another disadvantage of the braided type cord is that it is not very elastic because of the tightly braided-strands. Thus, packed portions of the braided cord tend to become dislodged as the dental practitioner continues to pack additional portions of the cord around the margin of the tooth. This tendency to dislodge, which is commonly referred to as "popping out," is caused by variations (i.e., having to pack the cord around high and low points) that are generally present within the floor of the sulcus adjacent the margin of the tooth as one moves around the periphery of the margin. Because of the lack of elasticity in the longitudinal dimension of braided cord, when the dental practitioner places downward pressure on one portion of the cord, other portions of the cord are pulled out of place. In come cases the cord will actually "pop out" of its position in the sulcus.

One further disadvantage of braided retraction cord is encountered when packing the cord around anterior or front teeth where the gingival tissue is thinner and more easily damaged on the labial (lip) side of the tooth. For instance, a braided cord that will adequately retract the sulcus on the lingual (tongue) side, because of its lack of elasticity in the transverse dimension, may overstretch the sulcus on the lip side of the tooth, thereby causing unacceptable damage to the sensitive gingival tissues. Accordingly, use of braided cord in connection with the front teeth becomes very difficult and cumbersome as several cords must be packed into some portions of the sulcus, while only one or two cords are packed into other portions of the sulcus.

In view of the foregoing, it will be appreciated that it would be a significant advancement in the field of gingival tissue management preparatory to the taking of impressions if an improved retraction cord could be provided that successfully avoided the aforementioned problems.

PRINCIPAL OBJECTS AND BRIEF SUMMARY OF THE INVENTION

In view of the foregoing problems experienced with the prior art type retraction cords, it is a primary object of the present invention to provide an improved retraction cord that will maintain its structural integrity (i.e., will not unravel or permit the packing instrument to slip between the strands of the cord) during packing, yet has characteristics of elasticity and resilience that avoid the tendency of packed cord to dislodge as additional portions of the cord are packed around a tooth.

It is another primary object of the present invention to provide an improved retraction cord capable of carrying relatively large amounts of chemical agent into the sulcus to aid in hemostasis and retraction of gingival tissues.

Yet another principal object of the present invention is to provide a retraction cord that will maintain its structural integrity while being packed, yet is not so rigid as braided cord that the dental packing instrument tends to slip off of the cord during the packing step.

A further important object of the present invention is to provide a retraction cord that is sufficiently elastic and resilient in both the longitudinal (i.e., lengthwise) and transverse (i.e., radial) dimensions that it can be easily stretched so that the cord can be made thinner when necessary, as in the case where a smaller diameter cord is needed to pack the sulcus around the lip side of front teeth.

Still another important object of the present invention is to provide a retraction cord that is sufficiently elastic and resilient that it can advantageously conform to various radial dimensions, thus permitting a single cord to be used to accomplish both vertical and horizontal retraction of gingival tissue in the area of the margin of the tooth.

These and other objects and features of the present invention will become more fully apparent from the following description and appended claims taken in conjunction with the accompanying drawings.

In accordance with the foregoing principal objects, the present invention is directed to novel methods and apparatus for retracting gingival tissue preparatory to making impressions used in constructing an artificial crown. A novel gingival retraction cord is constructed by a knitting process in contrast to the twisted-strand or braided-strand construction of conventional retraction cords. Although knitted retraction cord maintains its structural integrity during placement, it also has characteristics of resilience and elasticity that aid in packing the cord into the gingival sulcus and that assists in retraction of the gingival tissue. In addition, the knitted construction enhances the fluid-carrying capacity of the knitted retraction cord so that relatively large amounts of hemostatic and/or retracting agent are carried into the sulcus.

BRIEF DESCRIPTION OF THE DRAWINGS

In the accompanying drawings, which represent the best mode presently contemplated for carrying out the invention.

DETAILED DESCRIPTION OF THE PRESENTLY PREFERRED EMBODIMENTS OF THE INVENTION

Reference is next made to a detailed description of the presently preferred embodiments of the invention as illustrated in the drawings, in which like parts are designated with like numerals throughout.

Figure 9:
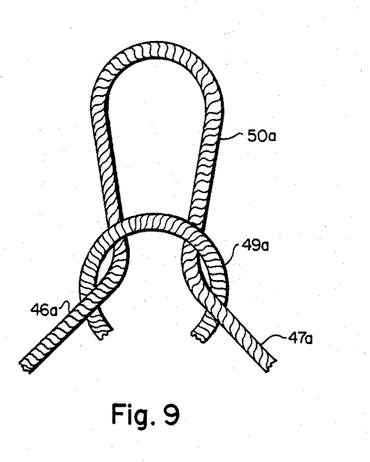
FIG. 9 illustrates an open-loop configuration used in knitting.
Figure 10:
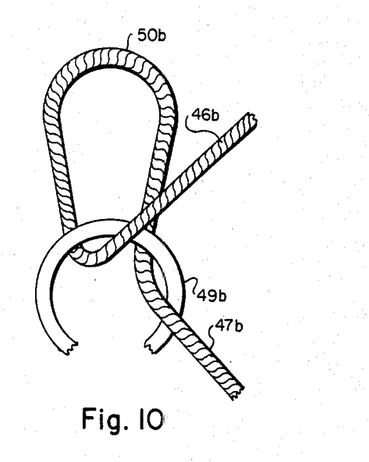
FIG. 10 illustrates a closed-loop configuration used in knitting.
Figures 11A, 11B:
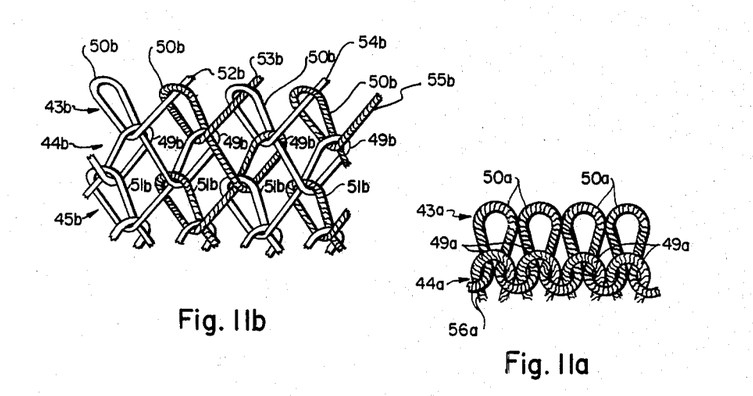
FIG. 11a schematically illustrates the manner in which a single strand of yarn can be knitted using the open-loop configuration of FIG. 9 so as to form a knitted retraction cord from a single strand.
FIG. 11b schematically illustrates the manner in which a plurality of strands may be interlocked using the closed-loop configuration of FIG. 10 so as to form a knitted retraction cord from several strands.

Reference is first made to FIGS. 9-11, which schematically illustrate two alternatives to the basic structure of the knitted retraction cord of the present invention. As used herein, "knitting" is defined as a process of using one or more separate strands to form a series of interlocking loops. A "strand" may comprise one or, alternatively, two or three threads (not shown) or yarns which are twisted together.

As illustrated in FIG. 9, one common type of loop that may be used to knit the retraction cord of the present invention is an "open" loop. The "open" loop is formed using a first loop 50a that is interlocked with an adjacent loop 49a such that the ends 46a and 47a of loop 50a do not cross one another. In contrast, FIG. 10 illustrates what is generally known as a "closed" loop because the end 46b bends back over and crosses in a manner that closes off the loop 50b.

FIG. 11a schematically illustrates two rows (generally designated at 43a–44a) of interlocked loops constructed utilizing the open-loop configuration of FIG. 9. As seen in FIG. 11a, row 43a comprises loops 50a, which are interlocked with the loops 49a of adjacent row 44a. FIG. 11a illustrates "weft" knitting, which is made from one loop to the next in the same course or row of loops, and which can be done using a single strand 56a.

FIG. 11b schematically illustrates three rows (generally designated at 43b–45b) of interlocked loops constructed utilizing the closed-loop configuration of FIG. 10. As seen in FIG. 11b, row 43b comprises loops 50b, which are interlocked with the loops 49b of adjacent row 44b. Loops 49b of row 44b are in turn interlocked with the loops 51b of adjacent row 45b, and so on. FIG. 11b illustrates "warp" knitting, in which several strands 52b-55b are connected such that the interlocking loops of each strand connect from one row to the next.

Figure 12:
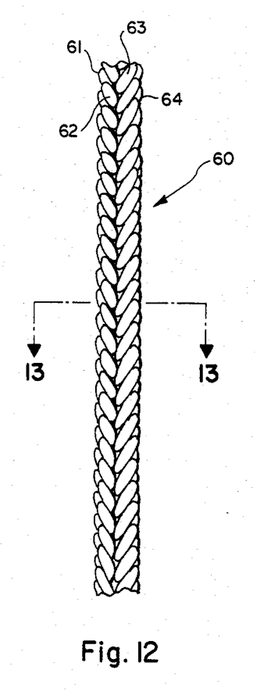
FIG. 12 illustrates a length of the knitted retraction cord of the present invention formed using four strands.

From the foregoing, it will be appreciated that it is possible to construct a knitted retraction cord 60 (see FIG. 12) using the open-loop or closed-loop pattern shown in FIGS. 9-11, or any other suitable knitting pattern. For example, FIG. 12 illustrates a typical knitted retraction cord 60 utilizing four strands of yarn 61-64 which are knitted together (see also FIG. 3) using the closed-loop pattern illustrated in FIGS. 10 and 11b.

The knitted retraction cord 60 is characteristically highly elastic and resilient in both the longitudinal and transverse dimensions. Thus, cord 60 can be easily stretched along its length, and it can also be easily squeezed or compressed radially as hereinafter more fully described. This is so because in a knitted cord the strand or strands are oriented so that a portion of each strand runs transversely, or at approximately right angles to the longitudinal axis of the cord, thus making the cord more compressible and also more stretchable along its length. In contrast, a twisted-strand or braided type cord has very little elasticity.

As mentioned above, the use of a braided retraction cord has been found advantageous over twisted-strand cords because the braided cord maintains its structural integrity under the force of the dental packing instrument and under the pressure exerted by the surrounding gingival tissue once the cord is packed into the sulcus. Surprisingly, use of a resilient knitted retraction cord has also been found very advantageous in retracting gingival tissue, despite the fact that its inherent elasticity and resilience might be thought to be detrimental.

Thus, longitudinal elasticity, or the ability to stretch the cord lengthwise, is extremely beneficial because it avoids the tendency for packed cord to be dislodged as additional cord is pushed into the sulcus around the margin of the tooth; as the cord is packed, the "stretch" in the knitted cord permits stress to be placed on the cord without causing already packed portions of the cord to be pulled out of the sulcus.

Figure 15:
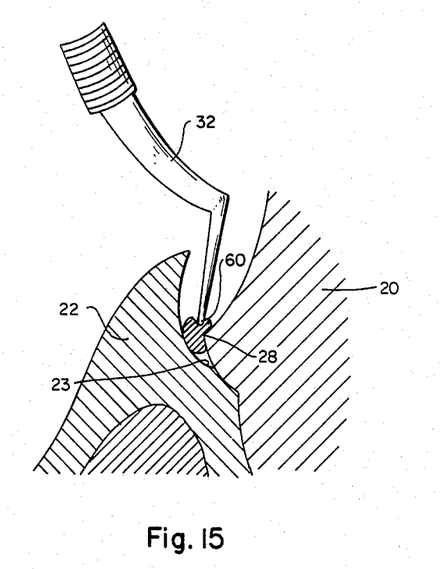
FIG. 15 schematically illustrates a portion of tooth and gingival tissue similar to FIG. 4, but showing the step of packing the knitted retraction cord of the present invention into the gingival sulcus.

Transverse resiliency, which can be characterized by the ability to radially compress and/or bend the cord 60, is also beneficial when packing the retraction cord into the gingival sulcus. Even if the loops of the knitted retraction cord are left rather loose, because of the intricate interlocking network, there is no tendency for the dental packing instrument to slip through the knitted cord. Rather, the compressibility of knitted cord 60 causes the cord 60 to "dimple" around the edges of the dental packing instrument 32 in the manner illustrated in FIG. 15. Comparing FIGS. 4 and 15, it will be appreciated that the dental packing instrument 32 will be much more likely to slip off the braided, nonresilient retraction cord 30 of FIG. 4 than it would be to slip off of the compressible, knitted cord 60 of FIG. 15.

As mentioned above, one of the chief advantages of braided retraction cord has been that braided cord is not deformed when packed into the sulcus. In contrast, twisted-strand cord tends to flatten out, thereby performing less efficient retraction. Thus, it might be expected that a compressible retraction cord would be disadvantageous. However, it has been found that knitted retraction cord is extremely beneficial for use in retracting gingival tissue, even though knitted cord is more resilient and thus compressible. First, because of its compressibility and bendability, there is less tendency to damage underlying gingival tissue as force is applied during packing of the cord; the force tends to be spread out over a larger area. Also, the transverse resilience of the knitted cord 60 enables it to conform (see FIG. 15) to irregularities within the sulcus. Thus, the knitted cord 60 can accomplish both horizontal and vertical retraction using a single cord.

Another advantage of knitted retraction cord is its tendency to return to its original uncompressed shape because of its resilience. Thus, when a knitted retraction cord is packed into the sulcus, it is compressed, and the "memory" in the retraction cord causes the cord to gently push outward against the gingival tissue. By selecting an appropriate diameter of knitted retraction cord, this outward pushing can significantly increase the ability of the knitted cord to retract gingival tissues over conventional retraction cord. In order to take advantage of this property, it is anticipated that when substituting knitted retraction cord for conventional twisted-strand or braided cord, the diameter of the knitted cord will be larger than the diameter of the conventional cord being replaced. Thus, whereas conventional retraction cord comes in sizes having a diameter in the range of about 0.4 to 1.0 millimeters, it is expected that knitted retraction cord will have a diameter in the range of about 0.75 to about 1.75 millimeters.

Yet another advantage arising from the compressibility of knitted retraction cord is realized when retracting gingival tissue from around the anterior or front teeth. The labial or lip-side gingival tissue around the anterior teeth is particularly thin and membranous; more so, for example, than the lingual or tongue-side gingival tissue of the anteriors. Thus, labial tissue is more susceptible to damage if it is stretched or retracted too far or too fast, resulting in fibrosis, sloughage and/or formation of scar tissue. Accordingly, it is preferable to avoid too much horizontal retraction. This is more readily accomplished using the knitted retraction cord of the present invention due to its transverse elasticity. The lingual gingival tissue can be adequately retracted with the knitted retraction cord only slightly compressed, and by virtue of its compressability and its ability to stretch and become thinner, the same cord can be packed into the sulcus on the labial side of an anterior tooth without over-retracting the gingival tissue. The cord then exerts a gentle, steady force on the tissue, which is desireable.

Figure 13:
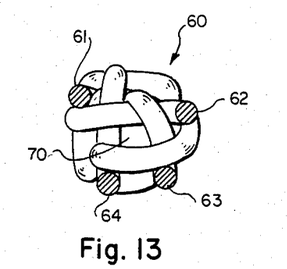
FIG. 13 illustrates a transverse section of the knitted retraction cord of FIG. 12, taken along the line 13—13 and drawn to a larger scale.
Figure 14:
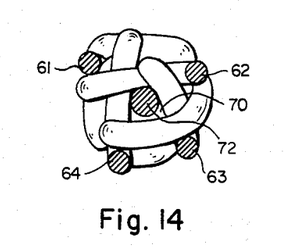
FIG. 14 illustrates a transverse section of retraction cord similar to the view of FIG. 13, but further comprising one or more longitudinal center strands.

Also, as seen in FIG. 13, the knitted retraction cord may have a hollow core 70. Choice of knitting techniques, the number of strands, and the diameter of strands all affect the size of the hollow core 70. The extent of transverse resilience is dependent to some extent on the size of the hollow core 70. Alternatively, it is possible to run one or more central strands 72 through the hollow core in the manner illustrated in FIG. 14. The strand 72 fills some of the space present in hollow core 70. Increasing or decreasing the diameter of central strand 72 can permit the transverse elasticity and longitudinal resilience to be easily controlled without adjusting the specifications of the knitted cord. Choice of an appropriate material for strand 72, e.g. wire, nylon, or yarn, etc., will also be useful in controlling the resilience of the knitted retraction cord.

Another beneficial result of the knitted retraction cord 60 is that the interlocking loops result in a substantially increased interstitial volume that is capable of carrying relatively large amounts of chemical retracting and hemostatic agent. Additionally, the ability of knitted retraction cord to effectively deliver the chemical retracting and hemostatic solution to the gingival tissue is greatly augmented by the fact that the knitted retraction cord is compressed when packed into the sulcus; thus, the cord actually expresses the hemostatic agent into the small capillaries of the tissue when it is compressed, thereby forcing the chemical agent into the bleeding pores to stop hemorrhage.

Since use of a chemical retracting and hemostatic agent is also very important in temporarily overcoming the natural elasticity of gingival tissue, the ability of knitted retraction cord to deliver relatively large amounts of such an agent into the sulcus is extremely advantageous. Not only does the enhanced administration of the retracting agent permit the knitted retraction cord to be removed after a shorter waiting interval, but it also results in more uniform administration of chemical agent and a more uniform retraction, thereby permitting a better impression to be taken. The improved liquid-carrying capacity of knitted retraction cord makes it feasible to utilize nonabsorbent man-made fibers in place of the absorbent cotton fibers necessary when utilizing twisted-strand or braided-strand retraction cords, if so desired.

Apart from improved retraction and hemostatic characteristics, knitted retraction cord is relatively easy to manufacture. It has been found that a knitting machine utilizing only a few strands of yarn (from 1 to 6) is capable of producing knitted retraction cord. Also, it is relatively easy to produce knitted cord having a circular cross section. This is advantageous because the desired amount of retraction will then be obtained regardless of the orientation of the cord in the sulcus.

From the foregoing, the manner of using the retraction cord of the present invention will be readily apparent to those of skill in the art. Thus, after a tooth has been prepared in the manner illustrated in FIG. 2, knitted retraction cord that has been soaked in an appropriate chemical solution containing a retraction agent and a hemostatic agent is packed into the sulcus. Alternatively, although less desirably, the knitted retraction cord may be pre-impregnated with a suitable chemical agent rather than soaking it prior to placement.

Although the knitted retraction cord may be left in place for up to twenty minutes (depending on the retracting agent used) without causing injury to sensitive gingival tissue, a much shorter period of time is generally sufficient to achieve the desired retraction illustrated in FIG. 8 when utilizing an appropriate chemical agent. When chemical agents such as aluminum chloride, or aluminum sulfate (alum) are used, impression material is usually injected into the sulcus concurrently with removal of the cord before blood from hemorrhaging tissues has an opportunity to seep into the sulcus. The use of knitted retraction cord is extremely advantageous when utilizing these solutions.

Alternatively, when utilizing a solution of ferric sulfate, such as that sold under the trademark ASTRINGEDENT by Ultradent Products Inc., Salt Lake City, Utah, it is not necessary to act with such split-second timing, and excellent impressions are more easily obtained. Thus, when utilizing ferric sulfate, the retraction cord is removed after an appropriate interval, and ferric sulfate solution is then applied directly to any tissue that is still bleeding in order to arrest all hemorrhaging, such as by use of the applicator sold under the trademark DENTO-INFUSOR, by Ultradent Products Inc. The tooth and sulcus are then washed and dried to insure that no foreign material will interfere with the taking of an accurate impression. Finally, the impression material is injected into the now clean, dry and retracted gingival sulcus. Since suitable retraction of the gingival tissues will be maintained for in excess of thirty minutes when utilizing this technique, there is no need for haste throughout this procedure, and the dental practitioner can take the time needed to insure that a good impression is made.

From the foregoing, it will be appreciated that the knitted retraction cord in accordance with the present invention offers significant advantages over conventional twisted-strand or braided-strand retraction cord. The stretch and bendability obtainable in knitted retraction cord avoids the tendency for packed cord to pop out as additional portions are packed around a tooth. Simultaneously, the compressibility of knitted retraction cord prevents the dental packing instrument from slipping off the cord because of the tendency for knitted retraction cord to "dimple" under pressure from the packing instrument. Compressibility has also been found extremely advantageous because it assists in retraction of the gingival tissues by gently pushing against the tissue, and because it can be stretched and compressed so as to more readily conform to difficult areas such as the sulcus on the labial side of anterior teeth.

Knitted retraction cord also has the ability to carry relatively large amounts of chemical solution containing hemostatic and/or retracting agent. Coupled with the compressibility of knitted retraction cord, this feature greatly augments the ability of knitted retraction cord to effectively deliver retracting and hemostatic agents to the gingival tissues.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A gingival retraction cord comprising at least one strand formed into a plurality of interlocking loops so as to form a knitted retraction cord for use in retracting gingival tissue preparatory to making an impression of a tooth that has been prepared for fitting of an artificial crown, said cord being knitted sufficiently loosely such that it is elastic in its longitudinal dimension so as to be able to be stretched, and resilient in its transverse dimension so as to be able to be compressed and conformed to the contour and shape of a gingival sulcus when being packed therein.

2. A gingival retraction cord as defined in claim 1 wherein said strand comprises an absorbent material.

3. A gingival retraction cord as defined in claim 1 wherein a hollow core is formed through the center of said cord.

4. A gingival retraction cord as defined in claim 3 further comprising at least one strand positioned coaxially through the center of said hollow core.

5. A gingival retraction cord as defined in claim 1 wherein said retraction cord is about 0.75 to about 1.7 millimeters in diameter.

6. A gingival retraction cord as defined in claim 1 comprising a plurality of strands of fiber which are knitted together.

7. A gingival retraction cord comprising a plurality of strands, each of said strands being formed into a plurality of interlocking loops such that the loops of each said strand are interlocked sufficiently loosely with the loops of another strand so as to form a knitted retraction cord which is longitudinally elastic so that it can be stretched along its length and which is transversely resilient so that said cord can be compressed and conformed to a gingival sulcus when packing said retraction cord into said gingival sulcus preparatory to making an impression of a tooth that has been prepared for fitting of an artificial crown.

8. A gingival retraction cord as defined in claim 7 wherein a hollow core is formed substantially through the center of said cord.

9. A gingival retraction cord as defined in claim 8 further comprising at least one strand positioned through the center of said hollow core.

10. A gingival retraction cord as defined in claim 9 wherein the diameter of said cord is in the range of about 0.75 to about 1.75 millimeters.

11. A gingival retraction cord as defined in claim 10 wherein said cord comprises at least four strands of fiber which are knitted together.

12. A method of retracting gingival tissue away from the margin of a tooth which has been shaped preparatory to receiving an artificial crown, said method comprising the step of inserting a knitted retraction cord between said gingival tissue and the margin of said tooth so as to horizontally and vertically retract said gingival tissue, said knitted retraction cord comprising at least one strand which is formed into a plurality of sufficiently loosely interlocking loops such that said knitted retraction cord will exhibit longitudinal elasticity and transverse resilience so as to facilitate effective placement of said cord.

13. A method as defined in claim 12 wherein said knitted retraction cord comprises a plurality of strands which are knitted together.

14. A method as defined in claim 12 wherein a hollow core is formed through substantially the center of said cord.

15. A method as defined in claim 14 wherein said knitted retraction cord comprises at least one strand positioned coaxially through the center of said hollow core.

16. A method as defined in claim 12 wherein the diameter of said knitted retraction cord is in the range of about 0.75 to about 1.75 millimeters.

17. A method as defined in claim 12 further comprising the step of impregnating said knitted retraction cord with a chemical retracting and hemostatic agent prior to placement of said retraction cord about the margin of said tooth.

18. A method of manufacturing a gingival retraction cord for use in retracting gingival tissue from the margin of a tooth that has been prepared for receiving an artificial crown, said method of manufacture comprising the step of knitting at least one strand so as to form a plurality of interlocking loops, thereby forming said knitted retraction cord, said cord being knitted sufficiently loosely such that it is elastic in its longitudinal dimension so as to be able to be stretched, and resilient in its transverse dimension so as to be able to be compressed and conformed to the contour and shape of a gingival sulcus when being packed therein.

19. A method as defined in claim 18 wherein said loops are interlocked so as to form a hollow core through substantially the center of said knitted cord.

20. A method as defined in claim 19 further comprising the step of inserting at least one strand through the center of said hollow core.

21. A method as defined in claim 18 wherein a plurality of strands are knitted together to form said knitted retraction cord.

22. A method as defined in claim 18 further comprising the step of impregnating said knitted retraction cord with a chemical retracting and hemostatic agent.

23. A method as defined in claim 18 wherein the diameter of the knitted retraction cord is in the range of about 0.75 to about 1.75 millimeters.

* * * * *

UNITED STATES PATENT AND TRADEMARK OFFICE
CERTIFICATE OF CORRECTION

PATENT NO. : 4,522,593

DATED : June 11, 1985

INVENTOR(S) : DAN E. FISCHER

It is certified that error appears in the above-identified patent and that said Letters Patent is hereby corrected as shown below:

Column 3, line 32, "twisted-strands" should be --twisted strands--
Column 3, line 59, "braided-strands" should be --braided strands--
Column 4, line 24, "come" should be --some--
Column 5, line 30, "assists" should be --assist--
Column 8, line 13, "twisted-strand" should be --twisted strand--
Column 8, line 17, "to 1.0" should be --to about 1.0--
Column 8, line 35, "compressability" should be --compressibility--
Column 8, line 39, "desireable" should be --desirable--
Column 12, line 30, "are" should be --is"

Signed and Sealed this

First Day of October 1985

[SEAL]

Attest:

DONALD J. QUIGG

*Attesting Officer*

*Commissioner of Patents and Trademarks—Designate*